(12) United States Patent
Reed et al.

(10) Patent No.: US 8,367,644 B2
(45) Date of Patent: Feb. 5, 2013

(54) METHODS AND COMPOUNDS USEFUL TO INDUCE APOPTOSIS IN CANCER CELLS

(75) Inventors: John C. Reed, Rancho Sante Fe, CA (US); Maurizio Pellecchia, San Diego, CA (US)

(73) Assignee: The Burnham Institute, La Jolla, CA (US)

( * ) Notice: Subject to any disclaimer, the term of this patent is extended or adjusted under 35 U.S.C. 154(b) by 50 days.

(21) Appl. No.: 12/900,319

(22) Filed: Oct. 7, 2010

(65) Prior Publication Data

US 2011/0111057 A1    May 12, 2011

Related U.S. Application Data

(62) Division of application No. 10/877,781, filed on Jun. 25, 2004, now Pat. No. 7,812,058.

(60) Provisional application No. 60/482,886, filed on Jun. 25, 2003.

(51) Int. Cl.
*A01N 37/18* (2006.01)
*A61K 33/24* (2006.01)

(52) U.S. Cl. ........................................ 514/154; 424/649

(58) Field of Classification Search ................... 514/743
See application file for complete search history.

(56) References Cited

U.S. PATENT DOCUMENTS

| | | | |
|---|---|---|---|
| 5,804,567 | A | 9/1998 | Cheng et al. |
| 6,114,397 | A | 9/2000 | Flack et al. |
| 6,608,107 | B2 | 8/2003 | Wong et al. |
| 7,432,304 | B2 | 10/2008 | Wang et al. |
| 2003/0008924 | A1 | 1/2003 | Wang et al. |

FOREIGN PATENT DOCUMENTS

| | | |
|---|---|---|
| WO | WO 01/72319 A1 | 10/2001 |
| WO | WO 02/097053 A2 | 12/2002 |
| WO | WO 2005/009434 A2 | 2/2005 |

OTHER PUBLICATIONS

Abou-Karam and Shier, "Inhibition of Oncogene Product Enzyme Activity as an Approach to Cancer Chemoprevention. Tyrosine-Specific Protein Kinase Inhibition by Purpurogallin from *Quercus* Sp. Nutgall," *Phytotherapy Res.* (1999), 13:337-340, John Wiley & Sons, Ltd.
Becattini et al., "Rational Design and Real Time, In-Cell Detection of the Proapoptotic Activity of a Novel Compound Targeting Bcl-$X_L$," *Chem. Biol.* (2004), 11:389-395, Elsevier Science Ltd.
Degterev et al., "Identification of Small-Molecule Inhibitors of Interaction between the BH3 Domain and Bcl-$x_6$," *Nature Cell Biol.* (2001), 3:173-182, Macmillan Magazines Ltd.
Gilbert et al., "Antiproliferative Activity of Gossypol and Gossypolone on Human Breast Cancer Cells," *Life Sci.* (1995), 57(1):61-67, Elsevier Science Ltd.
Khafif et al., "Quantitation of Chemopreventive Synergism between (−)-Epigallocatechin-3-Gallate and Curcumin in Normal, Premalignant and Malignant Human Oral Epithelial Cells," *Carcinogenesis* (1998) 19(3):419-424, Oxford University Press.
Kitada et al., "Discovery, Characterization, and Structure—Activity Relationships Studies of Proapoptotic Polyphenols Targeting B-Cell Lymphocyte/Leukemia-2 Proteins," *J. Med. Chem.* (2003), 46:4259-4264, American Chemical Society.
Liu et al., "Inhibition of Melanoma Growth and Metastasis by Combination with (−)-Epigallocatechin-3-Gallate and Dacarbazine in Mice," *J. Cell. Biochem.* (2001), 83:631-642, Wiley-Liss, Inc.
Lugovskoy et al., "A Novel Approach for Characterizing Protein Ligand Complexes: Molecular Basis for Specificity of Small-Molecule Bcl-2 Inhibitors," *J. Am. Chem. Soc.* (2002), 124(7):1234-1240, American Chemical Society.
Quintana et al., "Gossypol-Induced DNA Breaks in Rat Lymphocytes are Secondary to Cytotoxicity," *Toxicology Letters* (200), 117(10):85-94.
Shelly et al., "Structure-Activity Studies on Gossypol in Tumor Cell Lines," *Anti-Cancer Drugs* (2000), 11:209-216, Lippincott Williams & Wilkins.
Stein et al., "A Preliminary Clinical Study of Gossypol in Advanced Human Cancer," *Cancer Chemother. Pharmacol.* (1992), 30:480-482, Springer-Verlag.
Suganuma et al., "Synergistic Effects of (−)-Epigallocatechin Gallate with (−)-Epicatechin, Sulindac, or Tamoxifen on Cancer-Preventive Activity in the Human Lung Cancer Cells Line PC-9," *Cancer Res.* (1999), 59:44-47.
Tzung et al., "Antimycin A Mimics a Cell-Death-Inducing Bcl-2 Homology Domain 3," *Nature Cell Biol.* (2001), 183-191.
Van Poznak et al., "Oral Gossypol in the Treatment of Patients with Refractory Metastatic Breast Cancer: A Phase I/II Clinical Trial," *Breast Cancer Res.* (2001), 66:239-248, Kluwer Academic Publishers.
Wang, Jia-Lun et al., "Structure-Based Discovery of an Organic Compound that Binds Bcl-2 Protein and Induces Apoptosis of Tumor Cells," *PNAS* (2000), 97(13):7124-7129.
Wang, Xianghong, "Cytotoxic Effect of Gossypol on Colon Carcinoma Cells," *Life Sci.* (2000), 2663-2671, Elsevier Science Inc.
Wu, Dafang "An Overview of the Clinical Pharmacology and Therapeutic Potential of Gossypol as a Male Contraceptive Agent and in Gynaecological Disease," *Drugs* (1989), 38(3):333-341, ADIS Press Limited.
Yurtcu et al., "Apoptotic Effect of Gossypol on Human Lymphocytes," *Cell Biol. Int.* (2003), 791-794, Elsevier Science Ltd.
Zheng, Timothy S., "Death by Design: The Big Debut of Small Molecules," *Nature Cell Biol.* (2001), 3:E1-E3, Macmillan Magazines Ltd.

*Primary Examiner* — Sreeni Padmanabhan
*Assistant Examiner* — Timothy E Betton
(74) *Attorney, Agent, or Firm* — Wilson, Sonsini, Goodrich & Rosati

(57) ABSTRACT

The present invention provides a method for treating cancer in a mammal comprising contacting the cancer cells with a compound which is a apogossypol, derivative.

9 Claims, 12 Drawing Sheets

Figure 5: Activity of 6C1 and Gossypol as a single agent in previously untreated, newly diagnosed CLL Figure 6: Additive Effect of 6C1 and F-ara-A

Figure 9
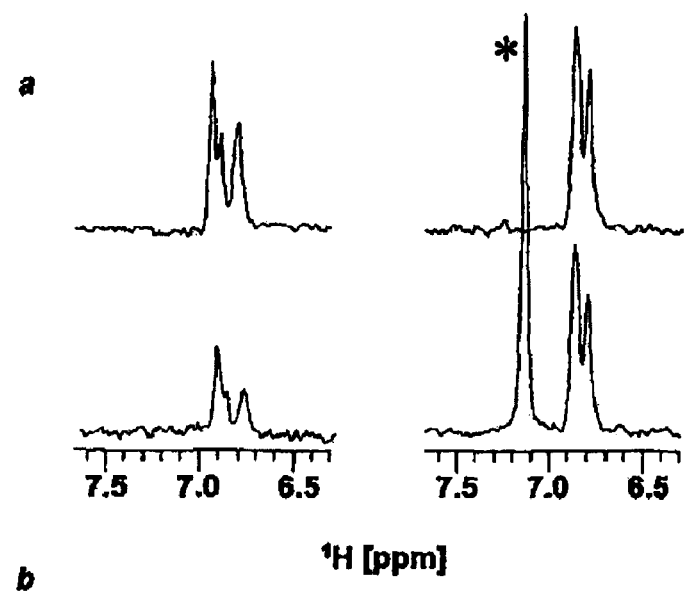
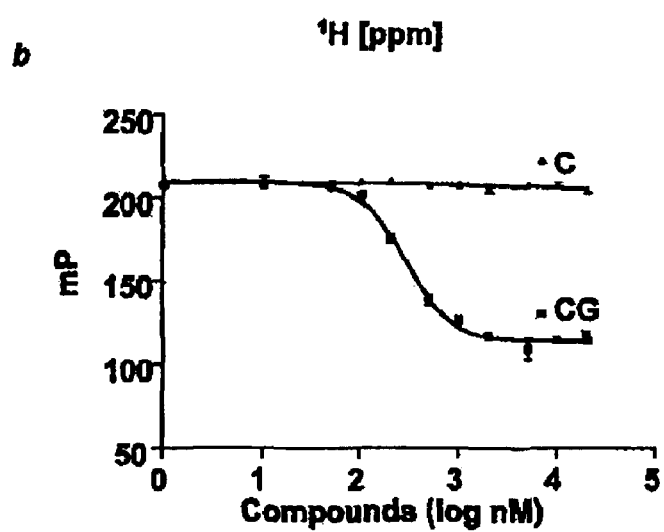

METHODS AND COMPOUNDS USEFUL TO INDUCE APOPTOSIS IN CANCER CELLS

CROSS REFERENCE TO RELATED APPLICATIONS

This application is a divisional application of U.S. application Ser. No. 10/877,781 filed Jun. 25, 2004, now issued as U.S. Pat. No. 7,812,058; which claims the benefit under 35 USC §119(e) to U.S. Application Ser. No. 60/482,886 filed Jun. 25, 2003, now expired. The disclosure of each of the prior applications is considered part of and is incorporated by reference in the disclosure of this application.

GRANT INFORMATION

This invention was made with government support under Grant No. CA78040-05 awarded by the National Institutes of Health. The government has certain rights in the invention.

BACKGROUND OF THE INVENTION

Currently, there is a need for novel, potent, and selective agents to prevent and or treat cancer, particularly melanoma, cancer of the cervix, or leukemia. One of the methods currently under study is selective induction of apoptosis. There is also a need for pharmacological tools for the further study of the physiological processes associated with selective induction of apoptosis.

Programmed cell-death (apoptosis) is critical for tissue homeostatis, for the physiological removal of unwanted cells during development and in host defence mechanism (Vaux et al., *Cell*, 96:245 (1999)). Inhibition of apoptosis is implied in every known human malignancy. This inhibition provides malignant cells with a selective growth advantage, allowing survival in the face of radiation or chemotherapy. (See Reed, *Curr Opin. Oncol.*, 7:541 (1995), and Kelekar et al., *Trends Cell. Biol.*, 8:324 (1998).) The Bcl-2 family of proteins are believed to be important regulators of apoptosis; pro-survival members of this family, such as Bcl-$x_L$, contain, on the surface, an hydrophobic groove in which is believed to allow binding of the BH3 domain of the pro-apoptotic counterpart (Johnstone et al., *Cell*, 108:153 (2002)). This binding is believed to be crucial for apoptosis regulation, in fact pro and anti-survival proteins can reverse each other function through dimerization. It is believed that the anti-apoptotic Bcl-2 family members are generally overexpressed in many human malignancies. These observations have lead to a growing interest in the discovery of small molecules, targeting anti-apoptotic proteins of the Bcl-2 family, and mainly, Bcl-$x_L$, as potential anticancer therapeutic agents (Wang et al., *Proc. Natl. Acad. Sci. U.S.A.*, 97:7124 (2000)), Degterev et al., *Nat. Cell Biol.*, 3:173 (2001); Tzung et al., *Nat. Cell Biol.*, 3:183 (2001); Enyedy et al., *J. Med. Chem.*, 44:4313 (2001)). However, until now the proposed compounds failed to fully corroborate the role of Bcl-$x_L$ inhibitors as potential anti-cancer agents (Kaneko et al., *Bioorg. Med. Chem. Lett.*, 11:887 (2001); Chin et al., *Angew. Chem. Int. Ed. Engl.*, 40:3806 (2001); Kutzki et al., *J. Am. Chem. Soc.*, 124:11838 (2002)) because of either their poor in vivo activity or the in vitro low affinity.

Therefore, a need exists to identify potent cell permeable compounds for targeting the Bcl-2 family of receptors such as, for example, Bcl-$x_L$, Bcl-2, Mcl-1, or Bcl-B. There exists a need for agonists that can inhibit the binding of BH3 to the Bcl-2 receptors.

In addition a need exists for compounds useful as chemosensitizers in particular for cancer types where anti-apoptotic Bcl-2 family proteins, such as Bcl-$x_L$, Bcl-2, Mcl-1, Bcl-W, or Bcl-B, are over produced by the cancer cells (such as, for example, lymphomas, neuroblastoma, breast cancer, lung cancer, prostate cancer, ovarian cancer, leukemias, and the like).

SUMMARY OF THE INVENTION

The present invention provides a method for treating cancer in a patient comprising contacting the cancer cells with a compound selected from the group consisting of gossypol, apogossypol, derivatives of apogossypol, theaflavin, theaflavin-3'-gallate, theaflavanin, (−) gallocatechin-3-gallate (GCG), (−) epigallocatechin-3-gallate (EGCG), (−) catechin-3-gallate (CG), (−) epicatechin-3-gallate (ECG), derivatives of purpurogallin, and mixtures thereof, effective to reduce the viability of the cancerous cells.

In addition, the present invention provides a method for inducing apoptosis, modulating caspase activity, or inducing cell death in a patient comprising contacting target cells with a compound selected from the group consisting of gossypol, apogossypol, derivatives of apogossypol, theaflavin, theaflavin-3'-gallate, theaflavanin, (−) gallocatechin-3-gallate (GCG), (−) epigallocatechin-3-gallate (EGCG), (−) catechin-3-gallate (CG), (−) epicatechin-3-gallate (ECG), derivatives of purpurogallin, and mixtures thereof, effective to induce apoptosis, modulate caspase activity, or induce cell death the target cells.

In addition, the present invention provides a method for inducing apoptosis, modulating caspase activity, or inducing cell death in cells that overexpress a Bcl-2 family protein comprising contacting target cells with a compound of the invention disclosed herein.

In another aspect, the present invention provides a method of treating cancer in a patient, comprising administering to the subject a chemosensitizing agent selected from the group consisting of gossypol, apogossypol, derivatives of apogossypol, theaflavin, theaflavin-3'-gallate, theaflavanin, (−) gallocatechin-3-gallate (GCG), (−) epigallocatechin-3-gallate (EGCG), (−) catechin-3-gallate (CG), (−) epicatechin-3-gallate (ECG), derivatives of purpurogallin, and mixtures thereof, in combination with an anticancer agent.

In addition, the invention provides a method for identifying a compound that is effective to modulate the binding of Bcl-2 proteins such as, for example, Bcl-$x_L$, Bcl-2, Mcl-1, Bcl-W, and Bcl-B to the BH3 domain of pro-apoptotic members of the Bcl-2 family proteins such as Bid, Bad, Bak, Bax or a peptide comprising a BH3 domain alone.

The invention provides methods for identifying a compound that binds to the Bcl-2 family proteins (e.g., Bcl-$x_L$, Bcl-2, Mcl-1, Bcl-W, and Bcl-B) or modulates a Bcl-2 activity. Furthermore, the invention provides a method for identifying a compound that binds the Bcl-2 family proteins or modulates a Bcl-2 activity, when complexed to the BH3 domain of pro-apoptotic members of the Bcl-2 family, proteins such as Bid, Bad, Bak, Bax or a peptide comprising a BH3 domain alone.

The invention provides a compounds as described herein for use in medical therapy (e.g., for use in inducing apoptosis, modulating caspase activity, inducing cell death, or treating cancer, preferably for use in treating lung cancer, breast cancer, prostate cancer, other forms of cancer, and leukemia, such as, for example, acute lymphocytic leukemia (ALL), acute myelogenous leukemia (AML), chronic myelogenous leukemia (CML), and other diseases of proliferation) as well as the use of a compound of formula I for the manufacture of a medicament for inducing apoptosis, modulating caspase activity, inducing cell death, or treating cancer, preferably for use in treating lung cancer, breast cancer, prostate cancer, CML, ALL, AML, other forms of cancer or leukemia, and other diseases of proliferation, in a mammal, such as a human. The compounds of the invention are also useful for treatment in diseases in which apoptosis, using the AHPN antagonist pathway, is one of the symptoms, such as, for example, heart conditions, Parkinson's disease, Alzheimer's disease and the like.

The invention also provides a method to induce apoptosis or death in a cell comprising contacting the cell, in vitro or in vivo, with an effective amount of a compound of the invention (as described herein).

The invention also provides a method to induce apoptosis in a mammal in need of such treatment comprising administering to the mammal, an effective amount of a compound of the invention (as described herein).

The invention also provides a method to activate a caspase (e.g., Capsase 3 and 7, via the inhibition the anti-apoptotic proteins in the Bcl-2 family) in a cell comprising contacting the cell, in vitro or in vivo, with an effective amount of a compound of the invention (as described herein).

The invention also provides a method for preventing or treating a pathological condition or symptom in a mammal, such as a human, associated with caspase (e.g., Capsase 3 and 7, via the inhibition the anti-apoptotic proteins in the Bcl-2 family) activation comprising administering to a mammal in need of such therapy, an effective caspase-modulating amount of a compound of the invention (as described herein).

The invention also provides a therapeutic method to induce cell death comprising contacting a cell, in vitro or in vivo, with an effective amount of a compound of the invention (as described herein).

The invention also provides a method to induce cell death in a mammal in need of such treatment comprising administering to the mammal, an effective amount of a compound of the invention (as described herein).

The invention also provides a method to treat cancer (e.g., lung cancer, colorectal cancer, breast cancer, prostate cancer, ALL, CLL, AML, solid tumors, other forms of cancer or leukemia such as, for example, lymphomas, neuroblastoma, and other diseases of proliferation) in a mammal in need of such treatment comprising administering to the mammal, an effective amount of a compound of the invention (as described herein).

The invention also provides a method of identifying an agent that inhibits the anti-apoptotic activity of the Bcl-2 family of proteins such as, for example, Bcl-$X_L$ and Bcl-2, comprising: a) detecting a selective Bcl-$X_L$ or Bcl-2 inhibitor bound to a labeled Bcl-$X_L$, said Bcl-$x_L$ inhibitor comprising a core structure selected from the group consisting of gossypol, apogossypol, derivatives of apogossypol, theaflavin, theaflavin-3'-gallate, theaflavanin, (−) allocatechin-3-gallate (GCG), (−) epigallocatechin-3-gallate (EGCG), (−) catechin-3-gallate (CG), (−) epicatechin-3-gallate (ECG), and derivatives of purpurogallin; b) contacting the bound Bcl-$X_L$ with a candidate agent, said candidate agent suspected of being able to inhibit Bcl-$X_L$; and c) detecting dissociation of said Bcl-$X_L$ inhibitor from said labeled Bcl-$X_L$, whereby said candidate agent is identified as an agent that inhibits Bcl-$X_L$.

(a) $T_{1\rho}$ experiments (200 ms relaxation time) with (−)EGCG before (upper spectrum) and after addition of 10 μM Bcl-$x_L$, (lower spectrum). Peaks shown in (a) represent the protons 4α and 4β of the catechin group, the * indicates DMSO;

(b) Results of Fluorescence Polarization-based competitive binding assay for (−) EGCG; and (c) Surface representation of Bcl-$x_L$ with the docked structure of (−)EGCG obtained by FlexX, the three subpockets (P1, P2 and P3) occupied by the ligand are indicated.

FIG. 9 illustrates a comparison between (−)CG and (−)C;

(a) $T_{1\rho}$ experiments (200 ms relaxation time) of (−)CG (left-side) and (−)C (right-side); spectra recorded in absence of protein are reported in blue; * indicates imidazole from protein buffer;

(b) Superposition of FPA results for (−)CG and (−)C; and (c) Surface representation of Bcl-$x_L$ binding pocked with the docked structures of (−)CG (red) and (−)C (blue).

Figure 10:
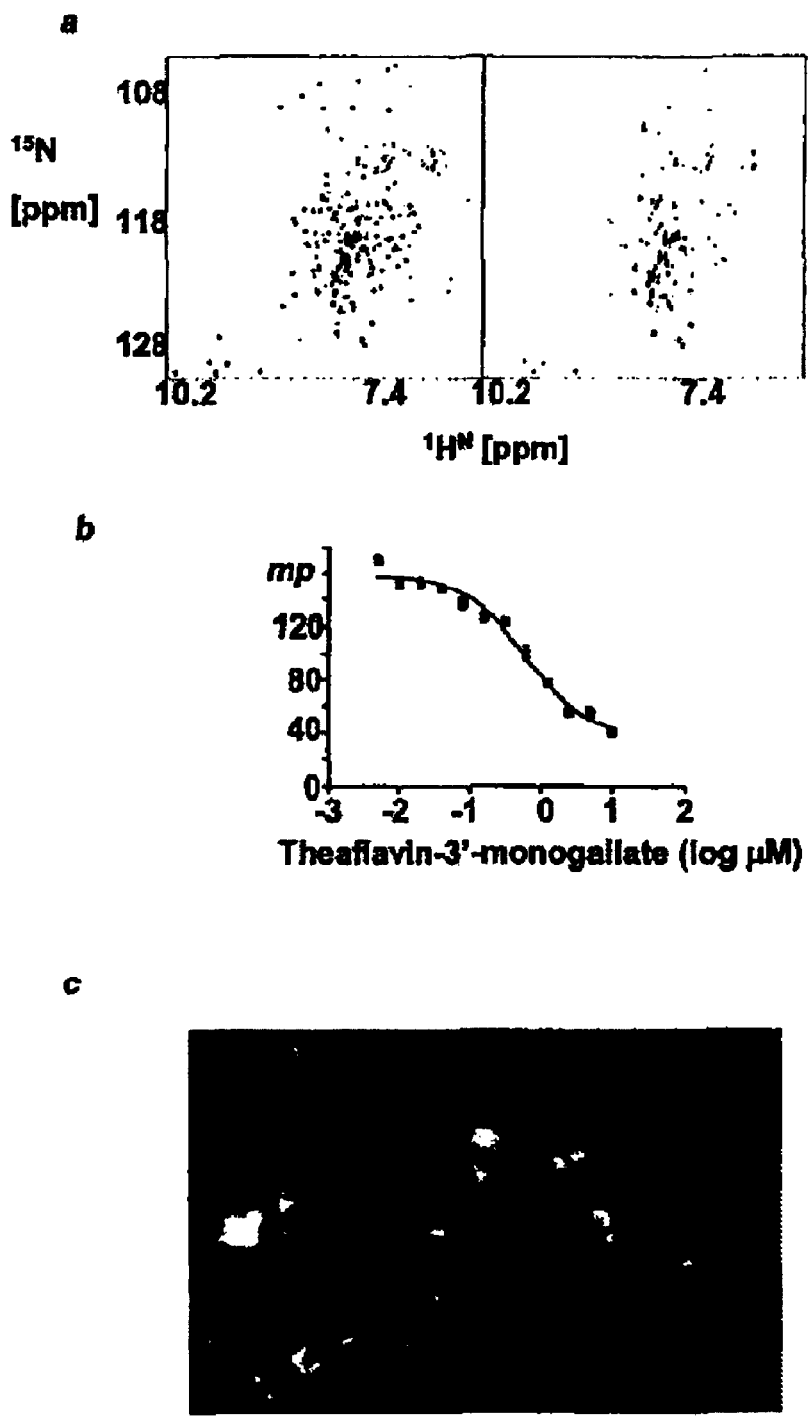
Figure 11:
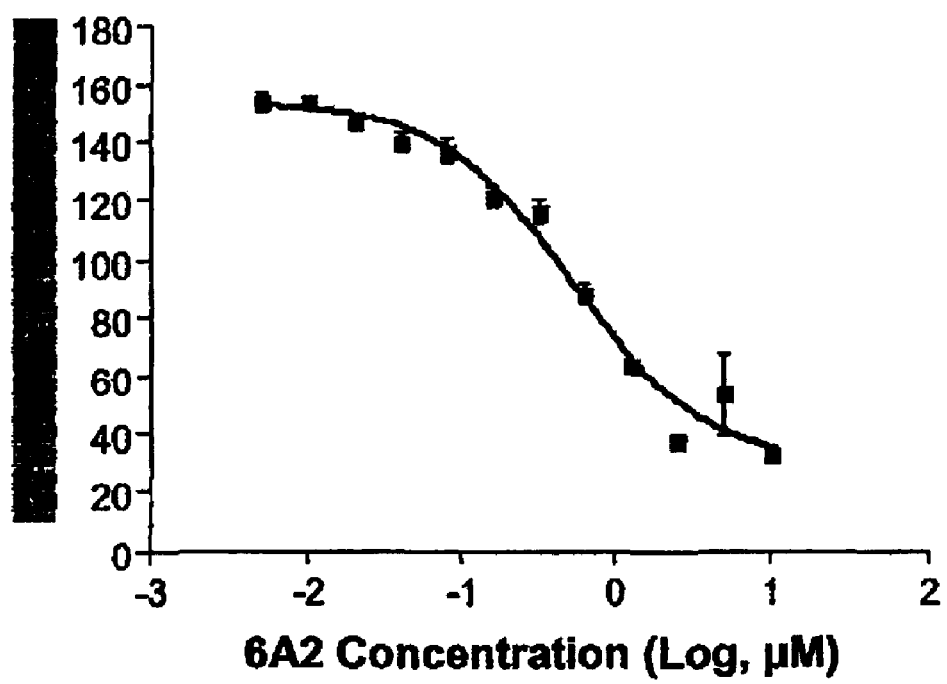

FIG. 10 illustrates the binding of Theaflavin-3'-gallate to the Bcl-$x_L$ receptor:

(a) 2D [$^{15}$N, $^1$H]-TROSY spectra for Bcl-$x_L$ (0.250 mM) before (left) and after addition of theaflavin-3' gallate (1 mM) (right);

(b) FPA results for theaflavin-3' gallate; and (c) Surface representation of Bcl-$x_L$ binding pocked with the docked structure of theaflavin-3' gallate, the three subpockets (P1, P2 and P3) occupied by the ligand are circled FIG. 11 illustrated the inhibition of Bcl-$x_L$ using Theaflavanin.

Figure 12:
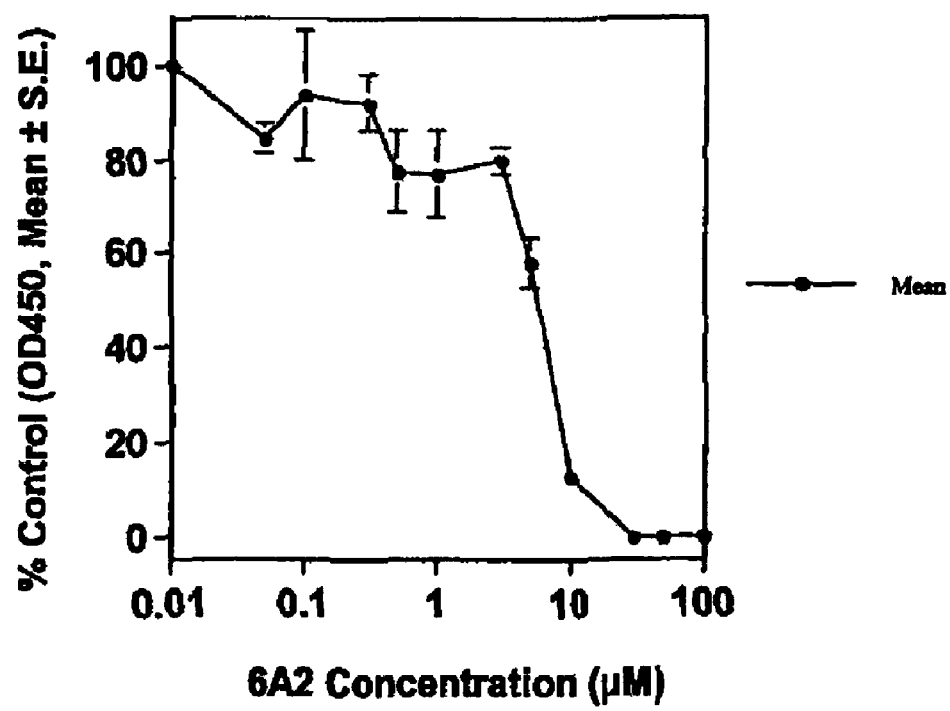

FIG. 12 illustrated the effect of Theaflavanin on Hela cells in an XTT assay.

DETAILED DESCRIPTION OF THE INVENTION

The compounds of the present invention are useful for antagonizing receptors of the Bcl-2 proteins (such as, for example, Bcl-2, Bcl-$x_L$, Mcl-1, Bcl-W, or Bcl-B). These proteins can render cancer cells more resistant to normal anticancer treatment such as, for example, radiation or chemotherapy. Thus, these cells do not die and can proliferate. Inhibition of such proteins by the compounds described herein would reduce or eliminate the cells' resistance to anticancer treatment. Therefore, these compounds are useful as chemosensitizers. Thus, the compounds of the invention can cause cancer cells to become more sensitive to anti-cancer treatment such as, for example, radiation or chemotherapy. Thus, the invention provides a method for modulating the formation of complexes between Bcl-2 proteins and the BH3 domain of pro-apoptotic Bcl-2 family members and compounds that are useful for modulating the amount or stability of these complexes.

The present invention provides a method for screening compounds using spectral techniques to determine the ability of the compounds of the invention to bind to the anti-apoptotic protein Bcl-$x_L$. The method identifies compounds that may be used in conjunction with other anticancer compounds. The different green and black tea polyphenol compounds were screened by using a combination of Nuclear Magnetic Resonance (NMR) binding assays, Fluorescence Polarization Assay (FPA) and Computational-Docking studies.

In one aspect, the invention provides a method to evaluate the activity of tea polyphenols that can act as anticancer agents partly through their binding to the anti-apoptotic protein Bcl-$x_L$ and subsequent inhibition of its interaction with pro-survival members of the Bcl-2 family.

In another aspect, the invention provides a method for identifying compounds that can effectively modulate the binding of Bcl-$x_L$ to BH3. The method includes (a) contacting Bcl-$x_L$ with BH3 under conditions suitable to form a Bcl-$x_L$-BH3 complex; (b) contacting the Bcl-$x_L$-BH3 complex with a test compound; and (c) determining the ability of the test compound to modulate the binding of Bcl-$x_L$ to BH3, where modulation of the binding of Bcl-$x_L$ to BH3 indicates that the test compound is an effective compound that modulates the binding of Bcl-$x_L$ to BH3.

In another aspect, the invention provides a method for identifying agents that can effectively modulate the binding of the Bcl-2 family proteins such as, for example, Bcl-$x_L$, Bcl-2, Mcl-1, Bcl-W, or Bcl-B comprising identifying a Bcl-2 inhibitor or a labeled Bcl-2 inhibitor, wherein the inhibitor is selected from the group consisting of the compounds listed in Tables 1, 2, 3 and apogossypol derivatives. The method includes (a) identifying a Bcl-2 inhibitor or a labeled Bcl-2 inhibitor, wherein the inhibitor is selected from the group consisting of gossypol, apogossypol, derivatives of apogossypol, theaflavin, theaflavin-35-gallate, theaflavanin, (−)-gallocatechin-3-gallate (GCG), (−) epigallocatechin-3-gallate (EGCG), (−) catechin-3-gallate (CG), (−) epicatechin-3-gallate (ECG), and derivatives of purpurogallin contacting the Bcl-2 family proteins with the inhibitor (e.g., those listed in table 1) under conditions suitable to form a complex with the Bcl-2 family protein; (b) contacting the Bcl-2 inhibitor complex with a test compound; and (c) determining the ability of the test compound to modulate the binding of Bcl-$x_L$ to the inhibitor, where modulation of the binding of the Bcl-2 protein to the inhibitor compound indicates that the test compound (agent) is an effective compound for modulating the binding of Bcl-2 to the inhibitor compound, In another aspect, the invention provides polyphenol compounds that are useful for sensitizing cancer cells to increase the effectiveness of traditional chemotherapy for the treatment of cancer.

In another aspect, the invention provides for the use of apogossypol, or an analog thereof, for the treatment of cancer either alone, or in combination with an anticancer agent.

In another aspect, the invention provides for the use of Purpurogallin, or an analog thereof, for the treatment of cancer either alone, or in combination with an anticancer agent.

In another aspect, the invention provides for the use of polyphenols from black or green tea for the treatment of cancer either alone, or in combination with an anticancer agent.

In another aspect, the invention provides for the use of polyphenols as a cancer prevention agent. The polyphenol compounds described in this invention may be administered to a patient with a high susceptibility to developing a cancer such as, for example, lung cancer, breast cancer, prostate cancer, colorectal cancer, and leukemia to reduce the likelihood that the patient will develop such cancer.

In the present invention, polyphenols from green and black tea were tested. Green tea is produced from the unfermented leaves of *Camelia Sinensis* and polyphenols—known as catechins—constitute its principal chemical components. Epicatechin (EC), epicatechin-3 gallate (ECG), epigallocatechin (EGC), and epigallocatechin-3 gallate (Table 1) are the major catechins contained in the green tea (Chu et al., In: Yamamoto, T., Juneja, J. R., Cu, D. C. and Kim, M. Chemistry and Application of Green Tea, pp. 13-22, New York: CRC Press, 1997). Black tea is made by extensive enzymatic oxidation of polyphenols to polymerized products, such as theaflavins (Pan et al.). Theaflavin, theaflavin-3 gallate, theaflavin-3' gallate, and theaflavin-3-3' digallate are the principal theaflavins in black tea.

In addition, the invention provides a method to correlate the anticancer activity of tea with its interaction with the anti-apoptotic proteins of the Bcl-2 family such as, for example, Bcl-$x_L$ and Bcl-2.

In addition, the invention provides a method to correlate the anticancer activity of tea with its interaction with the anti-apoptotic proteins of the Bcl-2 family such as, for example, Bcl-$x_L$ and Bcl-2.

In another aspect, the invention provides a method for screening compounds for anti-cancer activity and provides a method to determine that a compound of the invention can assist in cancer treatment using pharmacological models using the assays described herein below.

The invention also provides a pharmaceutical composition comprising the compounds described herein, or a pharmaceutically acceptable salt thereof, in combination with a pharmaceutically acceptable diluent or carrier. Further, the invention provides the use of compounds disclosed herein in combination with other known anticancer compounds.

The invention provides a method for treating cancer comprising administering to a mammal in need of such therapy, an effective amount of the compounds described herein, the compounds described herein in combination with an additional anti-cancer compound or a pharmaceutically acceptable salt thereof.

In addition, the invention provides a method for the prevention of cancer or a method for reducing the likelihood that a patient will develop such cancer comprising administering to a mammal in need of such therapy, an effective amount of the compounds described herein or a pharmaceutically acceptable salt thereof.

The following definitions are used, unless otherwise described: halo is fluoro, chloro, bromo, or iodo. Alkyl, alkoxy, alkenyl, alkynyl, etc. denote both straight and branched groups; but reference to an individual group such as "propyl" embraces only the straight chain group, a branched chain isomer such as "isopropyl" being specifically referred to. Aryl denotes a phenyl group or an ortho-fused bicyclic carbocyclic group having about nine to ten ring atoms in which at least one ring is aromatic. Heteroaryl encompasses a group attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$-$C_4$)alkyl, phenyl or benzyl, as well as a group of an ortho-fused bicyclic-heterocycle of about eight to ten ring atoms derived therefrom, particularly a benz-derivative or one derived by fusing a propylene, trimethylene, or tetramethylene digroup thereto.

Specifically, the term "alkyl" refers to a branched or unbranched saturated hydrocarbon group of 1 to 6 carbon atoms, such as methyl, ethyl, n-propyl, isopropyl, n-butyl, isobutyl, t-butyl, pentyl, and the like. Preferred alkyl groups herein contain 1 to 6 carbon atoms, such as, for example, methyl, ethyl, and the like.

As used herein the term "cycloalkyl" refers to a cyclic alkyl group of three to eight, preferably three, five or six, carbon atoms. The term "cycloalkylene" as used herein refers to a divalent cyclic alkylene group, typically a 3-, 5-, 6-, or 8-membered ring.

The term "alkoxy" as used herein refers to an alkyl group bound through a single, terminal ether linkage, i.e., an "alkoxy" group may be defined as —OR where R is alkyl as defined above. A "lower alkoxy" group refers to an alkoxy group containing 1 to 6, carbon atoms.

The term "aryl" as used herein intends an aromatic carbocyclic ring, typically 6- or 10-membered, wherein at least one ring is aromatic.

It will be appreciated by those skilled in the art that compounds of the invention having a chiral center may exist in and be isolated in optically active and racemic forms. Some compounds may exhibit polymorphism. It is to be understood that the present invention encompasses any racemic, optically active, polymorphic, or stereoisomeric form, or mixtures thereof, of a compound of the invention, which possesses the useful properties described herein. It being well known in the art how to prepare optically active forms (for example, by resolution of the racemic form by recrystallization techniques, by synthesis from optically active starting materials, by chiral synthesis, or by chromatographic separation using a chiral stationary phase) and how to determine the anti cancer activity using the standard tests described herein, or using other similar tests which are well known in the art.

Specific and preferred values listed below for groups, substituents, and ranges, are for illustration only; they do not exclude other defined values or other values within defined ranges for the groups and substituents.

Specifically, alkyl can be methyl, ethyl, propyl, isopropyl, butyl, iso-butyl, sec-butyl, pentyl, 3-pentyl, or hexyl; cycloalkyl can be cyclopropyl, cyclobutyl, cyclopentyl, or cyclohexyl; —O($C_1$-$C_6$)alkyl (alkoxy) can be methoxy, ethoxy, propoxy, isopropoxy, butoxy, iso-butoxy, sec-butoxy, pentoxy, 3-pentoxy, or hexyloxy.

Specific compounds useful for practicing the invention are listed in Table 1 and Table 2.

TABLE 1

| | GREEN TEA EXTRACTS | |
| --- | --- | --- |
| Compound | Structure | IC$_{50}$ (µM) |
| (−) Gallocatechin-3-gallate (GCG) | 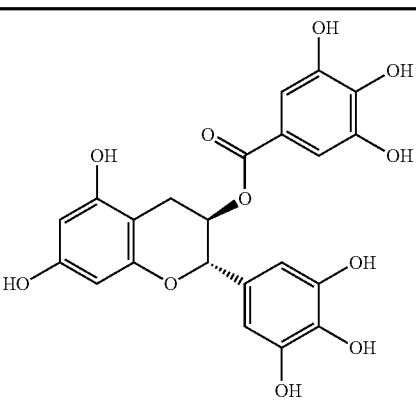 | 0.63 |

TABLE 1-continued

| GREEN TEA EXTRACTS | | |
|---|---|---|
| Compound | Structure | IC$_{50}$ (μM) |
| (−) Gallocatechin (GC) | | >100 |
| (−) Epigallocatechin-3-gallate (EGCG) | | 0.98 |
| (−) Epigallocatechin (EGC) | | >100 |
| (−) Catechin-3-gallate (CG) | | 0.29 |
| (−) Catechin (C) | | >100 |

TABLE 1-continued

GREEN TEA EXTRACTS

| Compound | Structure | IC$_{50}$ (μM) |
|---|---|---|
| (−) Epicatechin-3-gallate (ECG) | 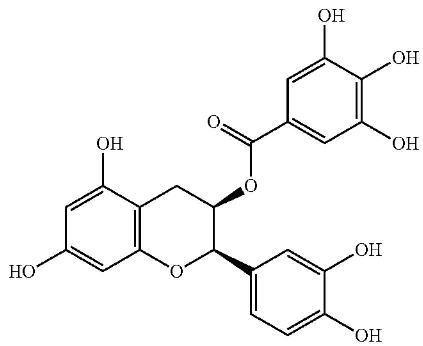 [SMILES: O=C(O[C@@H]1Cc2c(O)cc(O)cc2O[C@@H]1c1ccc(O)c(O)c1)c1cc(O)c(O)c(O)c1] | 0.24 |
| (+) Epicatechin (EC) | 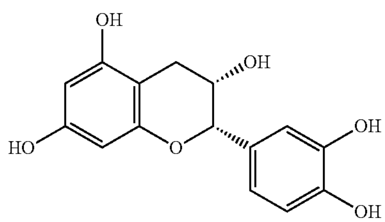 [SMILES: Oc1cc(O)c2c(c1)O[C@@H](c1ccc(O)c(O)c1)[C@@H](O)C2] | >100 |

TABLE 2

BLACK TEA EXTRACTS

| Compound | Structure | IC$_{50}$ (μM) |
|---|---|---|
| Theaflavin Digallate | 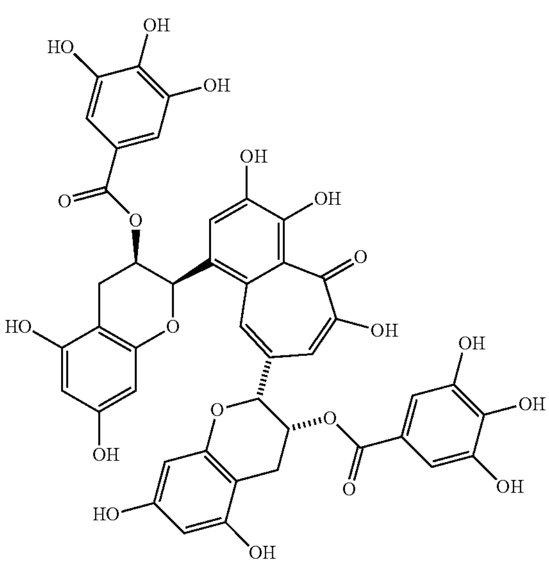 | >100 |

TABLE 2-continued
| BLACK TEA EXTRACTS | | |
|---|---|---|
| Compound | Structure | IC$_{50}$ (μM) |
| Theaflavin-3'-gallate | 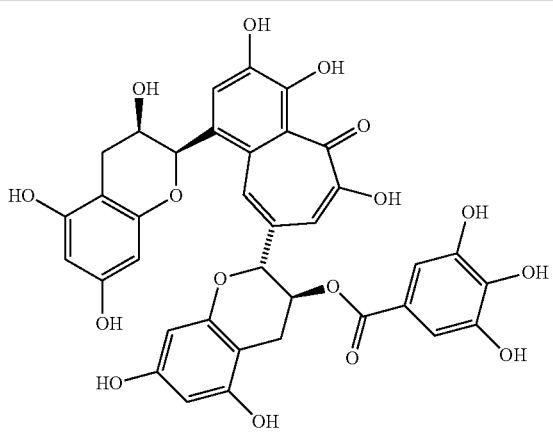 | 0.60 |
| Theaflavin | 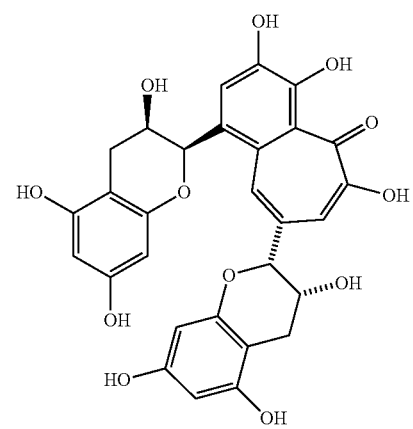 | 1.05 |
| Theaflavanin | 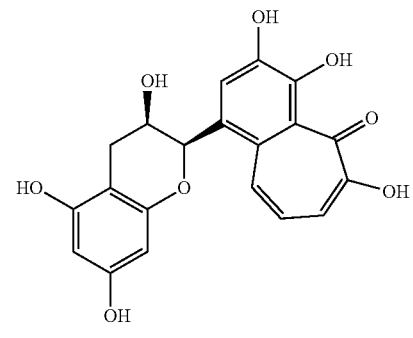 [SMILES: O=c1c(O)cccc2c([C@H]3Oc4cc(O)cc(O)c4C[C@H]3O)cc(O)c(O)c12] | 0.55 |

Non-limiting examples of polyphenols isolated from black or green tea include catechins, such as, Epicatechin (EC), epicatechin-3 gallate (ECG), epigallocatechin (EGC), epigallocatechin-3 gallate, and the like; theaflavins, such as, Theaflavin, theaflavin-3 gallate, theaflavin-3'-gallate, theaflavin-3-3' digallate and the like.

Other specific compounds of the invention include Purpurogallin and derivatives thereof such as shown in Table 3.

TABLE 3

Purpurogallin derivatives

[structure]

| CMPD | $R_1$ | $R_2$ | $R_3$ | $R_4$ | $R_5$ |
|---|---|---|---|---|---|
| Purpurogallin | —OH | —OH | —OH | —OH | —H |
| 5D1 | —H | —OH | —OH | —OH | —COOC$_2$H$_5$ |
| 1163 | —H | —OH | —OH | —OH | —COOCH$_3$ |
| 1142 | —H | —OH | —OH | —OH | —COOH |
| 6A1 | —OCH$_3$ | —OCH$_3$ | —OCH$_3$ | —OCH$_3$ | —H |
| 6A7 | —OCH$_3$ | —OCH$_3$ | —OH | —OCH$_3$ | —H |

Additional compounds useful in practicing the invention include compounds such as, for example, apogossypol, a compound which is less toxic to normal cells but has similar cytotoxicity against cancer cells as Gossypol, and analogues of Apogossypol. These analogues have improved potency and selectivity for Bcl-x1/2. The analogue compounds of the invention have the formula I:

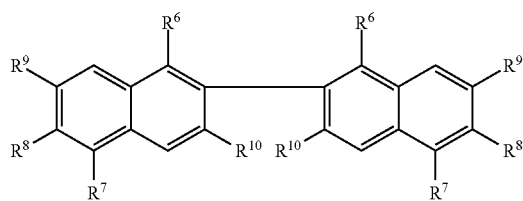

wherein: each $R^6$, $R^8$, $R^9$ and $R^{10}$ are independently hydrogen, hydroxyl, —(C$_1$-C$_6$)alkyl, —O(C$_1$-C$_6$)alkyl, —(C$_1$-C$_6$)alkylhalo, —OC(O)(C$_1$-C$_6$)alkyl, or halo; each $R^7$ is independently hydrogen, —(C$_3$-C$_8$)cycloalkyl, —(C$_6$-C$_{10}$)aryl, or —(C$_1$-C$_6$)alkyl(C$_6$-C$_{10}$)aryl; or a pharmaceutically acceptable salt thereof.

Specific $R^6$, $R^8$, $R^9$ groups are independently hydrogen, —OH, —OCH$_3$, —CF$_3$, —CH$_3$, —OC$_2$H$_5$, —OC(O)CH$_3$, F, Cl, or Br.

Specific $R^7$ groups are independently hydrogen, —C$_2$H$_5$; -i-Pr, n-Pr, n-Bu, t-Bu, i-Bu, s-Bu, cyclohexyl.

Specific $R^{10}$ groups are independently hydrogen, —OH, —OCH$_3$, —CF$_3$, —CH$_3$, —OC$_2$H$_5$, —OC(O)CH$_3$, F, Cl, or Br.

A specific compound of the invention has formula (I) where $R^6$, $R^8$, $R^9$, are each acetate (—OC(O)CH$_3$); $R^7$ is i-Pr; and $R^{10}$ is —CH$_3$ (Apogossypol hexaacetate). This compound can also be used as pro-drug for oral administration of apogossypol. In another embodiment the compounds of the invention include compounds of formula (I) wherein one of the $R^6$ groups is a group other than hydrogen.

As used herein, the term "patient" refers to organisms to be treated by the methods of the present invention. Such organisms include, but are not limited to, humans. In the context of the invention, the term "subject" generally refers to an individual who will receive or who has received treatment (e.g., administration of the compounds of the invention, and optionally one or more anticancer agents) for a disease characterized by overexpression of Bcl-2 family proteins (e.g., Bcl-x$_L$, Bcl-2, Mcl-1, Bcl-W, or Bcl-B).

As used herein, the terms "anticancer agent," or "chemotherapeutic anticancer agent" refer to any chemotherapeutic compounds, radiation therapies, and surgical techniques that are used in the treatment of cancer.

Anticancer agents useful for practicing the instant invention include cytotoxic agents or cancer chemotherapeutic agents. Non limiting examples, of cytotoxic agents useful in the practice of the invention include, without limitation, small molecules, polypeptides, peptides, peptidomimetics, nucleic acid molecules, cells and viruses. As non limiting examples, cytotoxic agents useful in the invention include cytotoxic small molecules, i.e., compounds that typically target a DNA associated process, such as, for example, doxorubicin, docetaxel, trastuzumab, cyclophosphamide, melphalan, mitomycin C, bizelesin, cisplatin, doxorubicin, etoposide, mitoxantrone, SN 38, Et 743, actinomycin D, bleomycin, TLK286, and the like; antimicrobial peptides such as those described further below; pro-apoptotic polypeptides such as caspases and toxins, for example, caspase 8; diphtheria toxin A chain, Pseudomonas exotoxin A, cholera toxin, ligand fusion toxins such as DAB389EGF, ricinus communis toxin (ricin); and cytotoxic cells such as cytotoxic T cells. See, for example, Martin et al., *Cancer Res.*, 60:3218 (2000); Kreitman et al., *Blood*, 90:252 (1997); Allam et al., *Cancer Res.*, 57:2615 (1997); and Osborne et al., *Cancer J. Sci. Am.*, 2:175 (1996).

Additional anticancer chemotherapeutic agents suitable for use in the present invention include, without limitation, taxanes such as docetaxel (Taxotere, Aventis Pharmaceuticals, Inc.; Parsippany, N.J.) and paclitaxel (Taxol, Bristol Myers Squibb; Princeton, N.J.); an anthracyclin such as doxorubicin, idarubicin, daunorubicin, and the like; an alkylating agent; a vinca alkaloid; an anti metabolite; a platinum agent such as cisplatin or carboplatin; a steroid such as methotrexate; an antibiotic such as adriamycin; a isofamide; or a selective estrogen receptor modulator; an antibody such as trastuzumab.

Doxorubicin is a commonly used cancer chemotherapeutic agent and can be useful, for example, for treating breast cancer (Stewart et al., In: "Cancer: Principles and Practice of Oncology" 5th ed., Chap. 19 (eds. DeVita, Jr., et al.; J. P. Lippincott 1997). In addition, doxorubicin has anti angiogenic activity (Folkman, *Nature Biotechnology*, 15:510 (1997); Steiner, "Angiogenesis: Key Principles Science, Technology and Medicine," pp. 449 454 (eds. Steiner et al.; Birkhauser Verlag, 1992)), which can contribute to its effectiveness in treating cancer.

Alkylating agents such as melphalan or chlorambucil are cancer chemotherapeutic agents useful in the combination treatment of the invention. Similarly, a vinca alkaloid such as vindesine, vinblastine or vinorelbine; or an antimetabolite such as 5-fluorouracil, 5-fluorouridine or a derivative thereof are cancer chemotherapeutic agents useful in the combination treatment of the invention.

Platinum agents are chemotherapeutic agents useful in the combination treatment of the invention. Such a platinum agent can be, for example, cisplatin or carboplatin as described, for example, in Crown, *Seminars in Oncol.*, 28:28 (2001). Other cancer chemotherapeutic agents useful in the combination treatment of the invention include, without limitation, methotrexate, mitomycin C, adriamycin, ifosfamide and ansamycins.

Cancer chemotherapeutic agents used for treatment of breast cancer and other hormonally dependent cancers also can be used as an agent that antagonizes the effect of estrogen, such as a selective estrogen receptor modulator or an anti estrogen. The selective estrogen receptor modulator, tamoxifen, is a cancer chemotherapeutic agent that can be used in the combination treatment of the invention for treatment of breast cancer (Fisher et al., *J. Natl. Cancer Instit.* 90:1371 (1998)).

Another type of therapeutic agent useful in the combination treatment of the invention is an antibody such as a humanized monoclonal antibody. Non-limiting examples include, the anti epidermal growth factor receptor 2 (HER2) antibody. Trastuzumab (Herceptin; Genentech, South San Francisco, Calif.) is another therapeutic agent that is useful in a conjugate of the invention for treating HER2/neu overexpressing breast cancers (White et al., *Annu. Rev. Med.*, 52:125 (2001)).

Another therapeutic agent useful in the invention also can be cytotoxic agents, which, as used herein, is any molecule that directly or indirectly promotes cell death.

Specific anticancer agents include Flavopiridol, Adriamycin (doxorubicin), VP16 (Etoposide), Taxol (paclitaxel), cisplatin and the like.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds useful in practicing the invention can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

Compounds of the invention can be labeled using methods known in the art. A preferred detectable group is a fluorescent group. Fluorescent groups typically produce a high signal to noise ratio, thereby providing increased resolution and sensitivity in a detection procedure. Preferably, the fluorescent group absorbs light with a wavelength above about 300 nm, more preferably above about 350 nm, and most preferably above about 400 nm. The wavelength of the light emitted by the fluorescent group is preferably above about 310 nm, more preferably above about 360 nm, and most preferably above about 410 nm.

The fluorescent detectable moiety is selected from a variety of structural classes, including the following non-limiting examples: 1- and 2-amino-naphthalene, p,p' diaminostilbenes, pyrenes, quaternary phenanthridine salts, 9-aminoacridines, p,p'-diaminobenzophenone imines, anthracenes, oxacarbocyanine, marocyanine, 3-aminoequilenin, perylene, bisbenzoxazole, bis-p-oxazolyl benzene, 1,2-benzophenazin, retinol, bis-3-aminopridinium salts, hellebrigenin, tetracycline, sterophenol, benzimidazolyl phenylamine, 2-oxo-3-chromen, indole, xanthen, 7-hydroxycoumarin, phenoxazine, salicylate, strophanthidin, porphyrins, triarylmethanes, flavin, xanthene dyes (e.g., fluorescein and rhodamine dyes); cyanine dyes; 4,4-difluoro-4-bora-3a, 4a-diaza-s-indacene dyes and fluorescent proteins (e.g., green fluorescent protein, phycobiliprotein).

The compounds can be radiolabeled, where the labeling group spontaneously emits a signal, or generates a signal upon the introduction of a suitable stimulus. Radiolabels, include atoms such as, for example, $^{13}C$, $^{15}N$, $^{19}F$, $^{1}H$ and the like.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

Figure 1:
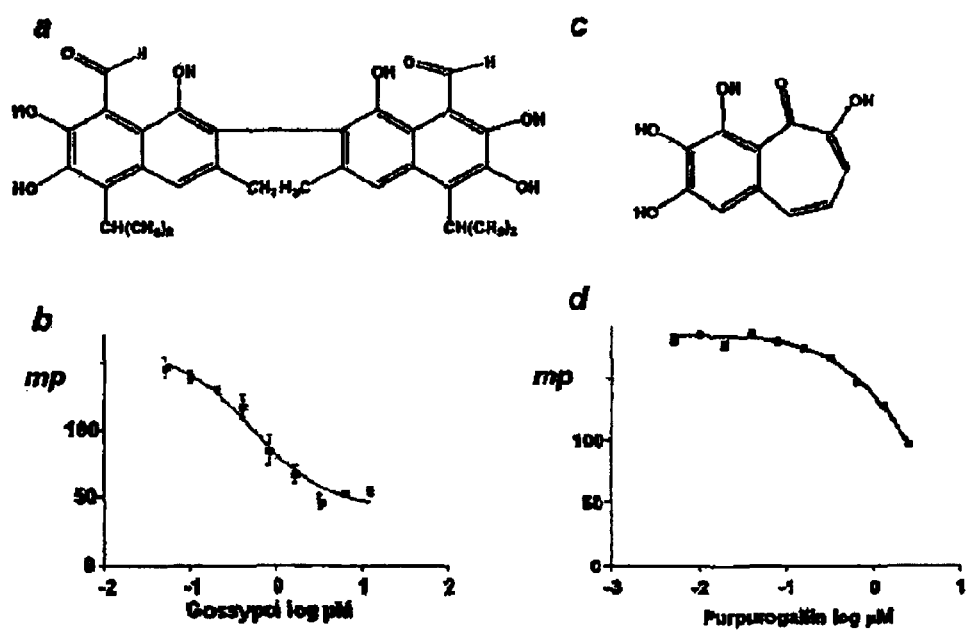
FIG. 1. Gossypol and Purpurogallin compete for the BH3-binding pocket of Bcl-xL. Chemical structure of Gossypol (a) and Purpurogallin (c). Results of Fluorescence polarization-based competitive binding assays (FPA) using a fluorescein-labeled Bad peptide (NLWAAQRYGRELRRMSD-K(FITC)-FVD) (SEQ ID NO:1) (Synpep Corporation, Dublin, Calif.) are shown in (b) for Gossypol and (d) for Purpurogallin.
Figure 2:
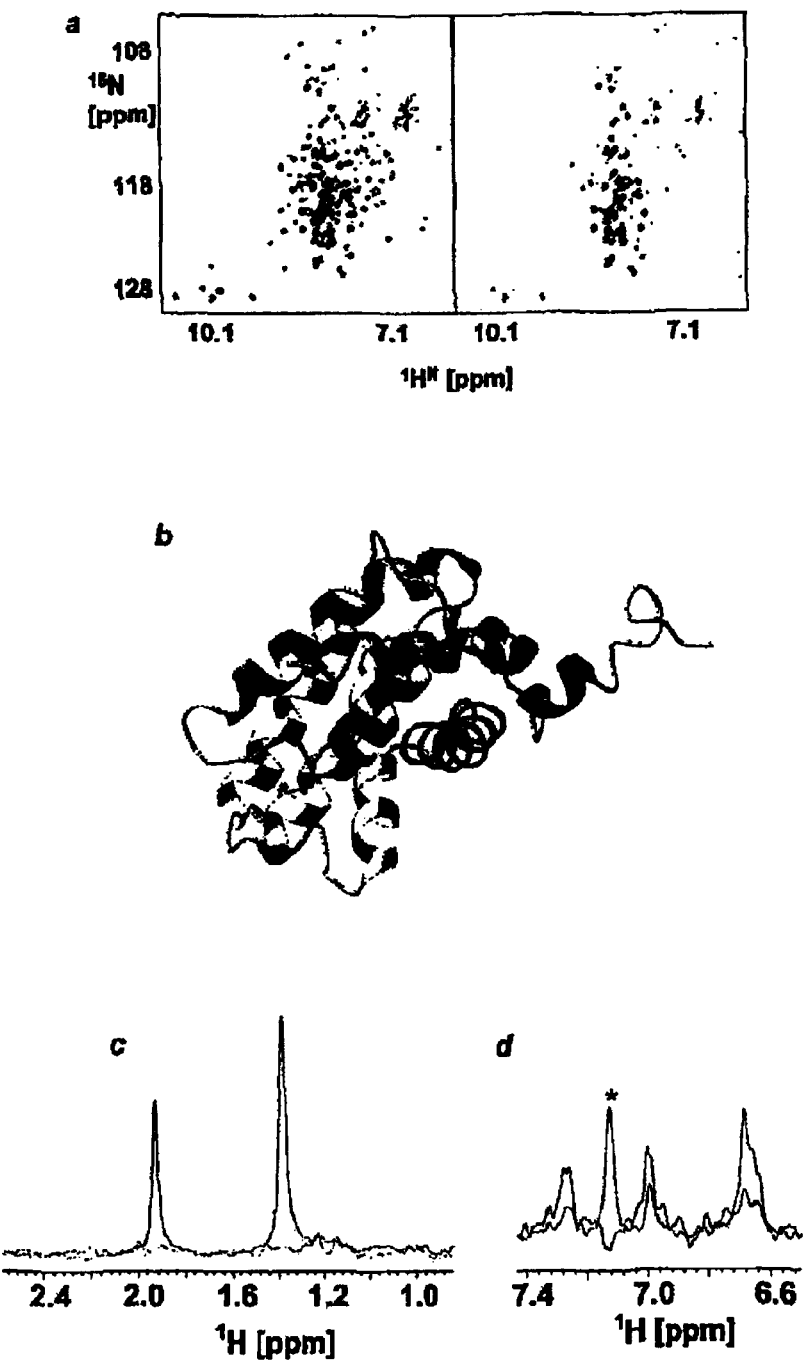
FIG. 2. NMR binding studies. (a) 2D [$^{15}$N,$^1$H]-TROSY spectra for Bcl-$x_L$ in the apo (left) and Gossypol-bound (right) forms, (b) Chemical-shift mapping of Gossypol into the three-dimensional structure of Bcl-$x_L$ in complex with Bak peptide (PDB code 1BXL). The peptide is displayed in yellow. Regions affected by the binding of Gossypol are colored in red. (c) and (d) $T_{1\rho}$ experiments (300 ms relaxation time) with Gossypol and Purpurogallin, respectively: blue, without protein and red with 10 μM Bcl-$x_L$. Peaks shown in (c) represent the isopropyl and the methyl groups in Gossypol. In (d), the peak marked with an asterisk represents residual imidazole present in the protein preparation.
Figure 3:
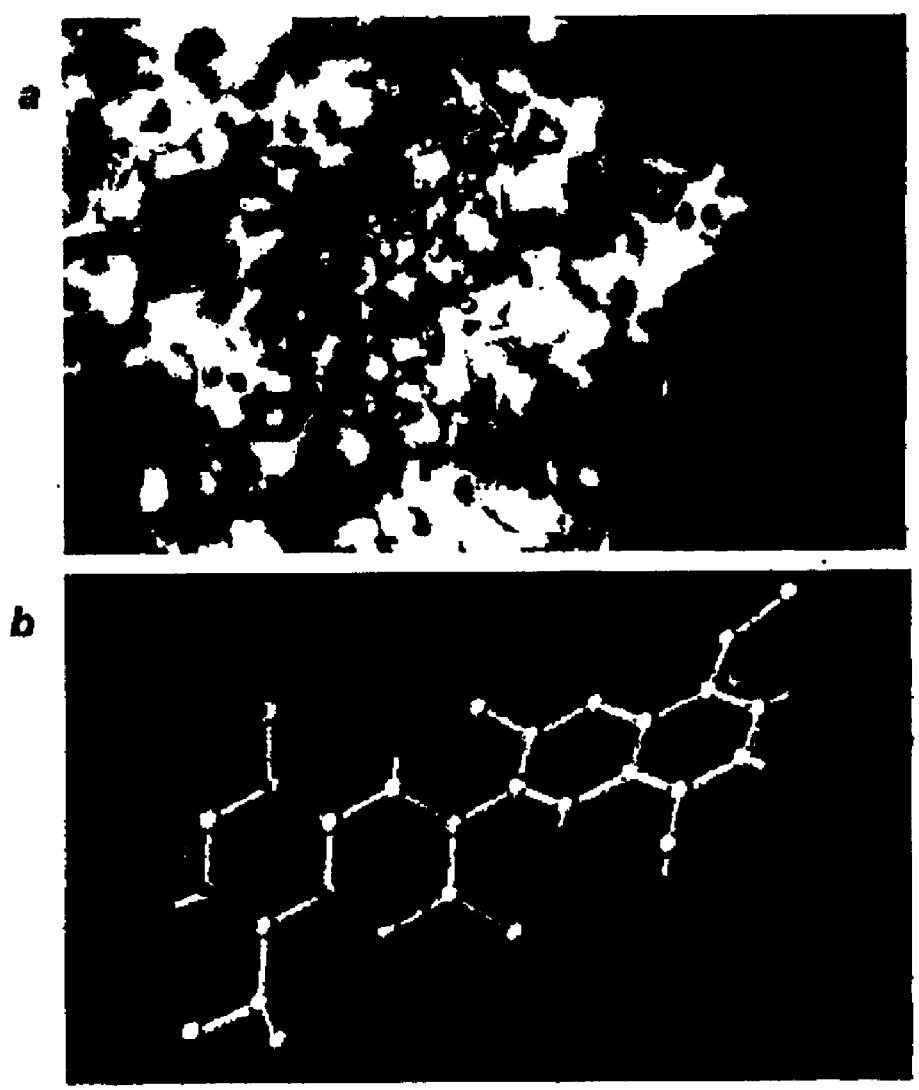
FIG. 3. Molecular modeling studies. (a) Surface representation of Bcl-$x_L$ with the docked structure of Gossypol obtained by FlexX. (b) Superposition of 5D1 (green) and Gossypol (white with red for oxygen atoms).

Docking studies with FlexX software (Kramer et al., *Proteins*, 37:228 (1999)) implemented in Sybyl (TRIPOS) using the Bcl-$x_L$ conformation found in the complex with Bak-peptide showed an optimal location for Gossypol in the deep hydrophobic cleft normally occupied by the Bak helical BH3 peptide in the complex (FIG. 3a). We docked both the (+) and the (−) stereoisomers of Gossypol, as these exhibited different activity in previous cell-based assays which showed that (−) Gossypol is ten times more effective than (+) Gossypol as a cytotoxic agent (Qiu et al., *Exp. Biol. Med.*, 227:398 (2002)). The goodness of the fit as measured by a scoring function (Pervushin et al., *Proc. Natl. Acad. Sci. U.S.A.*, 94:12366 (1997), and the intermolecular energy after minimization with the DOCK routine of Sybyl, was considerably better for (−) Gossypol (−32.7 Kcal/mol) versus (+) Gossypol (−25 Kcal/mol), in agreement with these observations. The structure of (−) Gossypol is shown (FIG. 3a), but the overall positioning of both stereoisomers of Gossypol is very similar.

Figure 4:
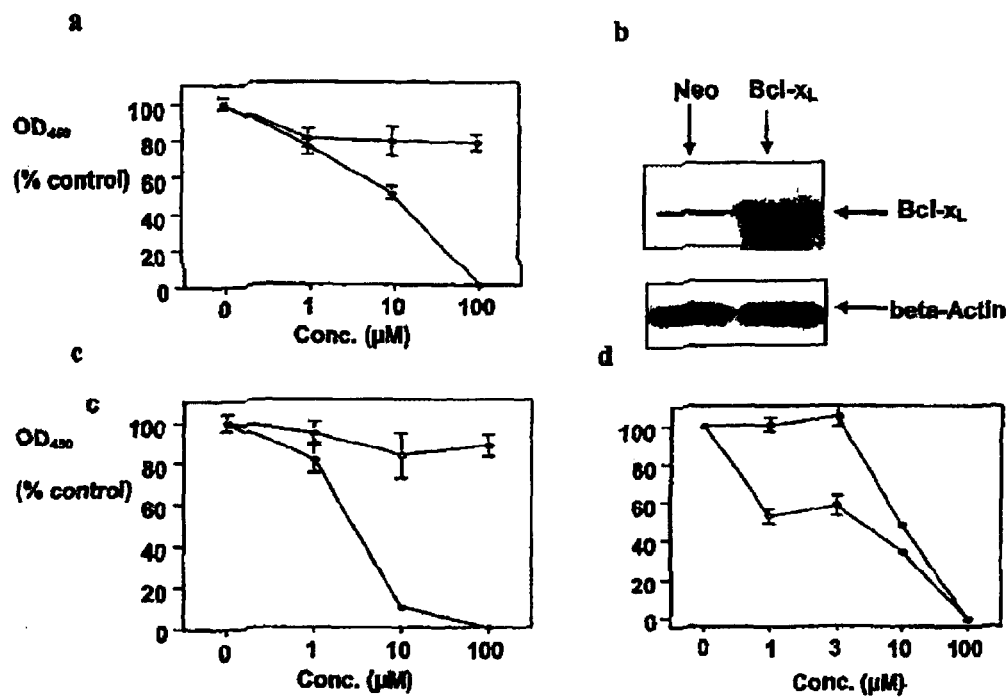
FIG. 4. Inhibitory effect of compounds on cancer cell survival. The effects of Gossypol on viability of tumor cells in culture were monitored by using XTT assays with (a) MCF7 and (b) ZR75-1 cell lines (black circles). As a negative control, a generic polyphenolic compound was also tested (open circles). Low-passage HeLa cells (between passage number 10 and 20) were transfected with pcDNA3-Bcl-$x_L$ (black circles) or control pcDNA3 plasmids (open circles), (c) Immunoblot analysis confirmed over-expression of Bcl-$x_L$ in the cells transfected with pcDNA3-Bcl-$x_L$, compound to pcDNA3-control transfectants. (Cell lysates were normalized for total protein content; 25 μg per lane). (d) HeLa-transfectants were treated with various doses of Gossypol (0, 1, 3, 10 and 100 μM). Data shown represent mean±standard deviation (n=4).
Figure 5:
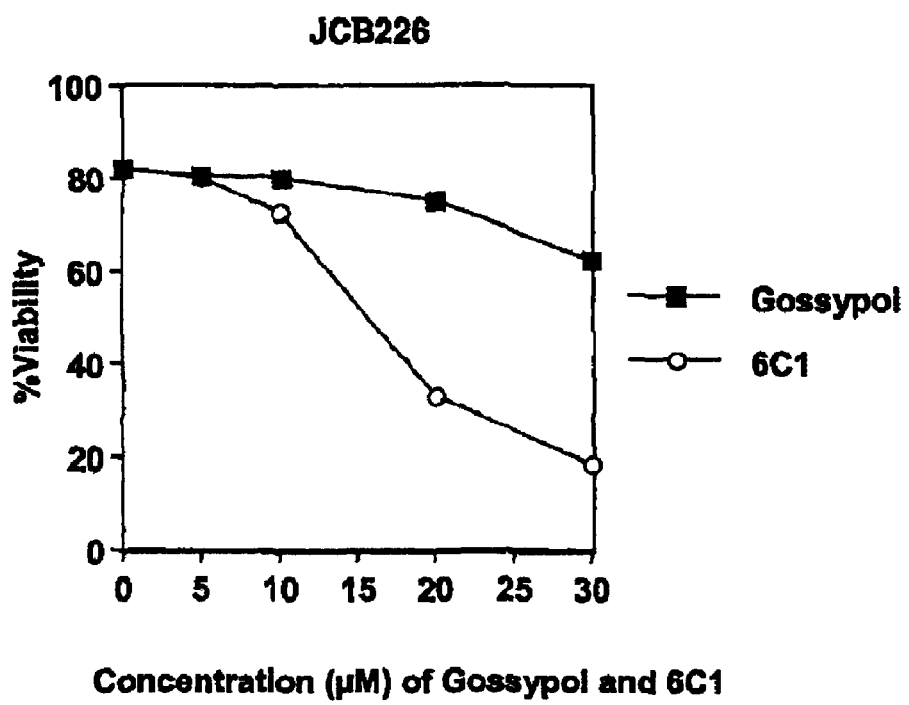
FIG. 5 illustrates the activity of Apogossypol (6C1) and Gossypol as a single agent in previously untreated, newly diagnosed CLL.
Figure 6:
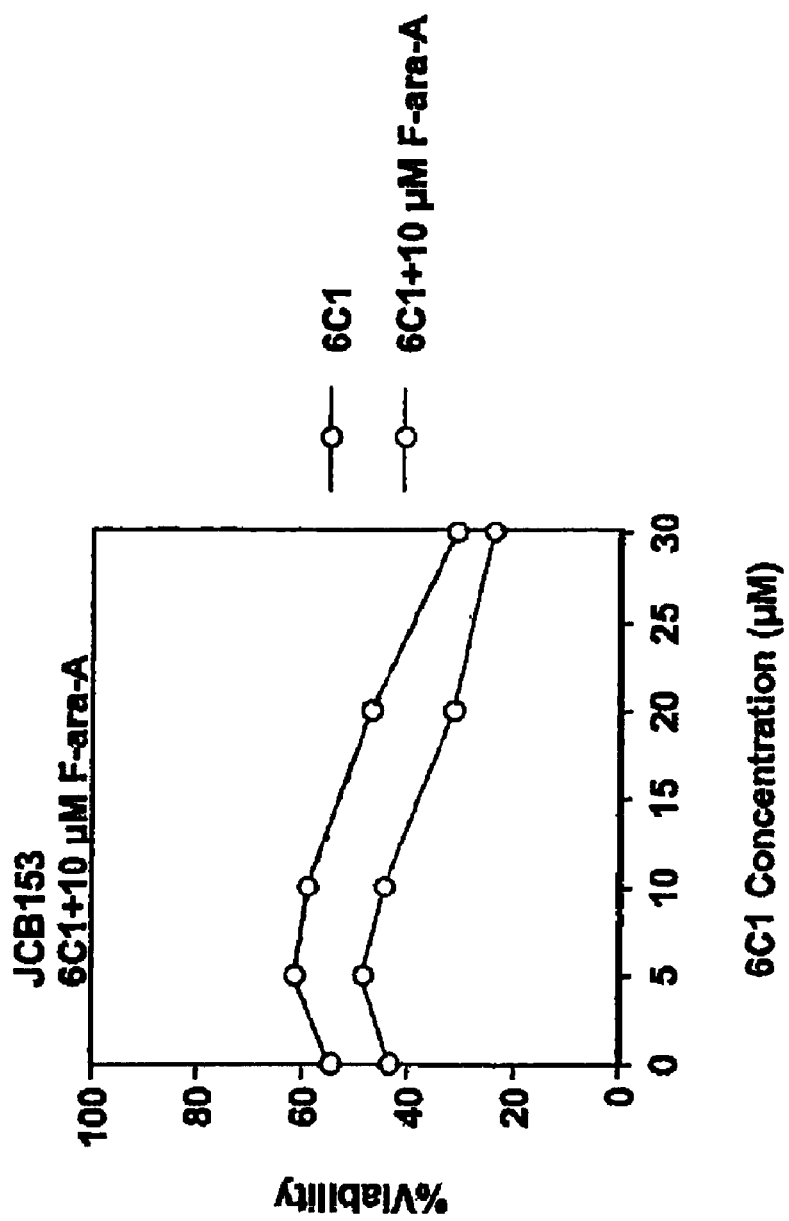
FIG. 6 illustrates the additive effect of Apogossypol (6C1) and fludarabine (F-ara-A).
Figure 7:
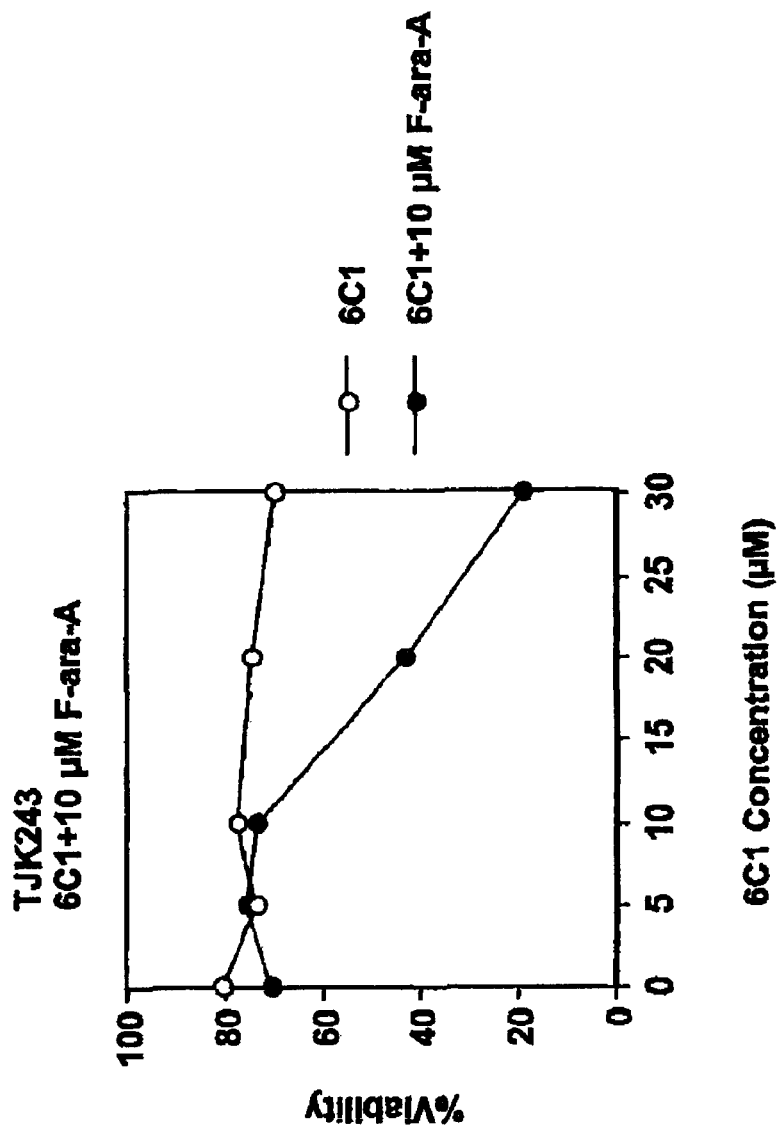
FIG. 7 illustrates the synergistic Effect of Apogossypol (6C1) with F-ara-A.
Figure 8:
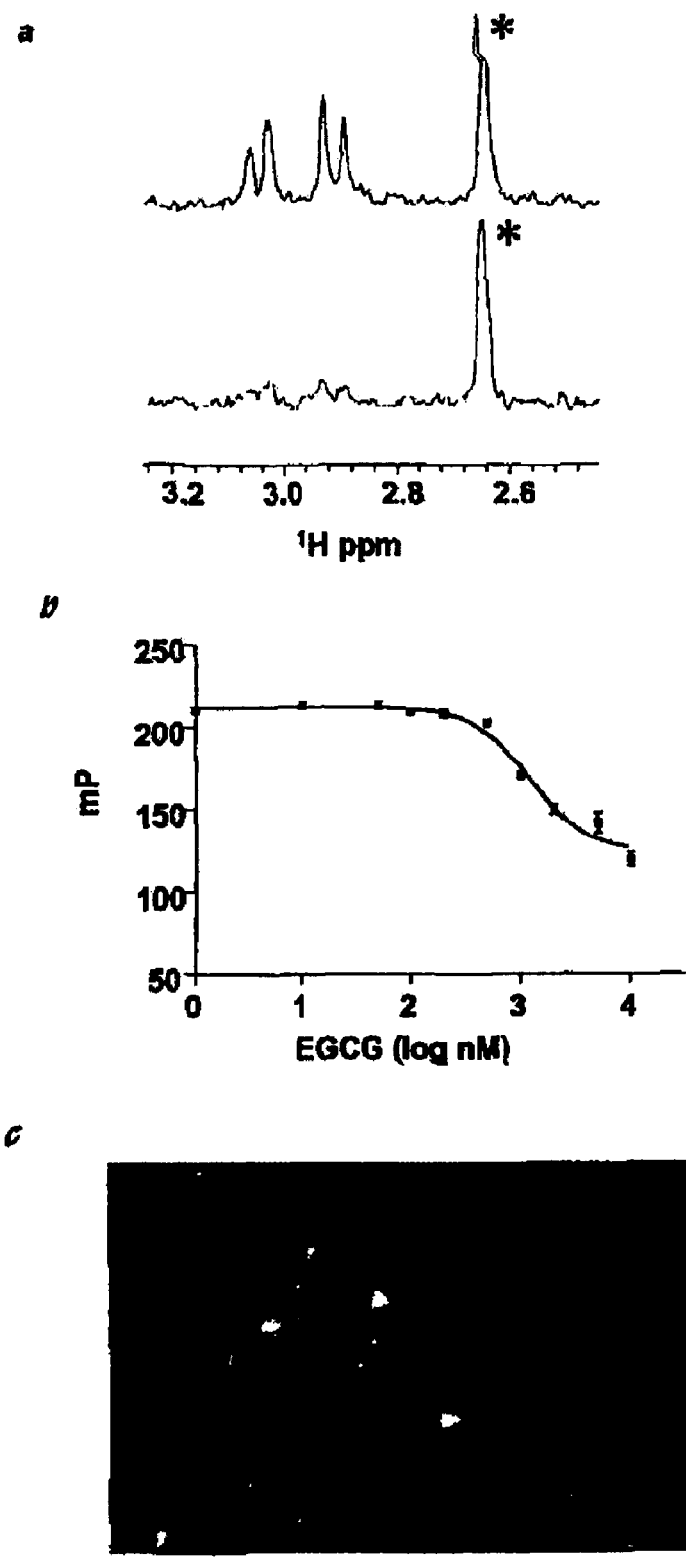
FIG. 8 illustrates the binding of (−)EGCG to the Bcl-$x_L$ receptor.

To evaluate the cytotoxic activity of our compounds on human tumors cells, we tested their biological activities using XTT dye reduction assays using two breast cancer cell lines: MCF7 (high expressor of Bcl-2/Bcl-$x_L$) and ZR75-1 (low expressor of Bcl-2/Bcl-$x_L$). Gossypol is a cytotoxic agent for MCF7 and ZR75-1 cells, (FIG. 4 a,b), reducing cell viability in a dose-dependent manner, with $IC_{50}$ values of 13.2 μM and 8.4 μM, respectively. Purpurogallin, however, did not show appreciable activity in these assays, potentially due to its hydrophilic character (ClogP ~0.7). Consistent with this observation, a Purpurogallin derivative 5D1 that is predicted to have better cell-membrane permeability properties (based on its ClogP of ~2.5) reduced cell viability in a dose-dependent manner, with $IC_{50}$ value of ~50 μM the ZR75-1 cell line (not shown). For these reasons, we further evaluated the cellular activity of our compounds in HeLa cells (Table 4), which are known to be less selective for compounds uptake. The inhibition data obtained with HeLa cells viability assays parallel the in vitro binding data with Bcl-$x_L$ (Table 4), with a correlation coefficient of r=0.9 (p=0.001).

EXPERIMENTAL SECTION

Fluorescence polarization assays (FPA). FPA assays were conducted with a fluorescein-labeled Bad peptide (NL-WAAQRYGRELRRMSD-K(FITC)-FVD) (SEQ ID NO:1) (Synpep Corporation, Dublin, Calif.) using a LJL Analyst HT (Molecular Devices Co., Sunnyvale, Calif.). Dilution buffer for all stocks and samples was 50 mM Tris-Bis pH 7.4, 0.01% bovine gamma globulin. A series of two-fold dilutions of Gossypol were prepared, i.e., 100 µM, 50 µM, down to 0.1 µM in dilution buffer. To each tube was added a solution containing 30 nM of Bcl-$x_L$ and 4 nM fluoresceinated peptide. The tubes were incubated for 5 minutes at room temperature and 20 µl each of reaction mixture was transferred to 96-well black PS, HE Microplate (LJL Biosystems Co.). All assays were performed in quadruplicate, with blank wells receiving no Gossypol. Then, the plate was read for total intensity and polarization (in mP units) was measured. Controls included dose-responses measurements in absence of the proteins, to assess any interactions between the compounds and the FITC-BH3 peptide. Eventual effects were taken into account by subtraction.

NMR Spectroscopy. 2D [$^{15}$N, $^1$H]-TROSY (Pervushin et al., *Proc. Natl. Acad. Sci. U.S.A.*, 94:12366 (1997); Pellecchia et al., *Nat. Rev. Drug Disc.*, 1:211 (2002)) spectra for Bcl-$x_L$ were measured with 0.5 mM samples of $^{15}$N-labeled Bcl-$x_L$. $^{15}$N-labeled and unlabeled Bcl-$x_L$ were prepared and purified as described in Sattler et al., *Science*, 275:983 (1997). For chemical-shift mapping and docking studies we used the three-dimensional structure of Bcl-$x_L$ in complex with Bak peptide (PDB code 1BXL). In addition to chemical-shift mapping with labeled proteins, $T_{1\rho}$ measurements (Hajduk et al., *J. Am. Chem. Soc.*, 119:12257 (1997)) and saturation transfer experiments such as WaterLOGSY experiments (Dalvit et al., *J. Biomol. NMR*, 18:65 (2000)) were also performed to further validate the binding of the studied compounds to Bcl-$x_L$. All experiments were performed with a 500 MHz Varian Unity+ spectrometer or a 600 MHz Bruker Avance600 spectrometer, both equipped with four rf channels and z-axis pulse-field gradients. Selective water saturation was performed with a train of selective IBURP2 pulses of 7 ms durations spaced by a 10 ms delay. Total saturation time used was 2.5 s. $T_{1\rho}$ series were measured with a spin-lock pulse of variable length. Measurements were then performed with 1 ms, 10 ms, 50 ms, 150 ms, 200 ms, 250 ms and 300 ms spin-lock time with 100 µM compounds in the absence and presence of 10 µM protein. In all experiments, de-phasing of residual water signals was obtained with a WATERGATE sequence.

Molecular Modelling. Molecular modelling studies were conducted on several R12000 SGI Octane workstations with the software package Sybyl version 6.9 (TRIPOS). The docked structure of Gossypol was initially obtained by FlexX (Kramer et al., *Proteins*, 37:228 (1999)) as implemented in Sybyl. Two calculations were performed. In the first, all binding-site torsion angles were kept fixed, while in the second side-chain torsion angles were free to change. The average scoring function for the 30 best solutions was only slightly lower when the side-chains were free to rotate. The position of the side-chains in the model did not change substantially from the initial values. The scoring function for (+) Gossypol was inferior to (−) Gossypol, but the overall positioning of both steroisomers was very similar. The resulting best scoring structures were subsequently energy minimized by using the routine DOCK of SYBYL keeping the site rigid. The energy of the ligands after the DOCK minimization was within 5 Kcal/mol from their global minimum of energy. Superposition of compounds was obtained by the routine MULTIFIT of SYBYL. Colour figures showing three-dimensional structures were prepared with the programs SYBYL and MOLMOL (Koradi et al, *J. Mol. Graph.*, 14:29; 14:51 (1996)).

Inhibitory Effect of Compounds on Cancer Cell Survival. The effects of the compounds studied in this paper on viability of tumor cells in culture were monitored by using XTT (Weislow et al., *J. Natl. Cancer Inst.*, 81:577 (1989)) assays with MCF7 and ZR75-1 cell lines. MCF7 cells were grown in DMEM containing 10% fetal bovine serum, penicillin/streptomycin, supplemented with $10^{-10}$ M insulin, 1 mM sodium pyruvate and glutamine. ZR75-1 cells were grown in RPMI containing 10% fetal bovine serum, penicillin/streptomycin, supplemented with HEPES buffer, 1 mM sodium pyruvate and glutamine. Cells were regularly tested for mycoplasma contamination. Cells were seeded triplicates at an initial cell density of 1,000 cells per well. Blank wells received no cells. Gossypol, Purpurogallin and 5D1 were added at final concentrations of 0, 1, 10 and 100 µM and incubated for three days. Relative numbers of viable cells was determined by XTT assay. Briefly, in a 96-well plate, we added 50 µl of a mixture of 1 mg/ml of XTT (Weislow et al., *J. Natl. Cancer Inst.*, 81:577 (1989)) (2,3-bis(2-methoxy-4-nitro-5-sulfophenyl)-5-[(phenylamino)carbonyl]-2H-tetrazolium hydroxide) (Polysciences, Washington, Pa.) containing 0.025 mM PMS (phenazine methosulfate) to each well. The 96-well plates were re-incubated for an additional 4 hours to allow for XTT formazan production. Then, the contents of each plate were mixed and optical densities were determined at a wavelength of 450 nm ($OD_{450}$). Net $OD_{450}$ was determined after subtracting $OD_{450}$ of blank wells. Low-passage HeLa cells (between passage number 10 and 20) were transfected with pcDNA3-Bcl-$x_L$ or control pcDNA3 plasmids using Lipofectamine Plus reagent (Invitrogen) and selected in medium containing 800 µg/ml of G418. Immunoblot analysis of Bcl-$x_L$ was accomplished as described (Krajanski 1996-Cancer Res) HeLa-transfectants were treated with various doses of Gossypol, Purpurogallin, and its derivatives (0, 1, 3, 10 and 100 µM).

Chemicals. Pure polyphenols were obtained from SIGMA (Gossypol and Purpurogallin) and/or from Microsource Discovery Systems (Purpurogallin derivatives). Reference compounds were obtained from Chembridge Corp. (San Diego). Gossypol was tested as a racemic mixture of (+) and (−) isomers. Compounds were dissolved in DMSO at 100 mM concentration and stored at −20° C. NMR analysis was periodically performed on the compounds as a quality control, prior to further dilution for binding and displacement assays. Reactivity of Gossypol was tested with a $^{15}$N-labeled test protein (BIR3 domain of XIAP). A solution containing 1 mM Gossypol and 200 µM $^{15}$N-labeled BIR3 was incubated for two hours and the [$^{15}$N, $^1$H]-correlation spectrum was recorded and compared with the spectrum of the apo-Bir3. No appreciable differences in the spectra were observed.

TABLE 4

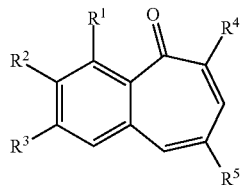

| CMPD | R₁ | R₂ | R₃ | R₄ | R₅ | IC$_{50}$ (μM) (Bcl-x$_L$) | IC$_{50}$ (μM) HeLa |
|---|---|---|---|---|---|---|---|
| Purpurogallin | —OH | —OH | —OH | —OH | —H | 2.2 | 6.5 |
| 5D1 | —H | —OH | —OH | —OH | —COOC$_2$H$_5$ | 73 | 51.5 |
| 1163 | —H | —OH | —OH | —OH | —COOCH$_3$ | 2.6 | ~30 |
| 1142 | —H | —OH | —OH | —OH | —COOH | 7.4 | 22.9 |
| 6A1 | —OCH$_3$ | —OCH$_3$ | —OCH$_3$ | —OCH$_3$ | —H | >100 | >100 |
| 6A7 | —OCH$_3$ | —OCH$_3$ | —OH | —OCH$_3$ | —H | >100 | >100 |

Structure Activity Relationships (SAR) of Purpurogallin Derivatives

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

---

---

What is claimed is:

1. A method of treating cancer in a subject, comprising administering to the subject a chemosensitizing agent selected from the group consisting of gossypol, apogossypol, derivatives of apogossypol, in combination with an anticancer agent wherein said cancer is selected from lung cancer, breast cancer, prostate cancer, colorectal cancer, and leukemia.

2. The method of claim 1 wherein the derivative of apososspol is a compound having formula (I):

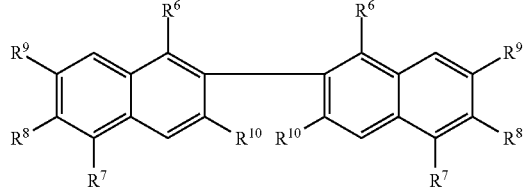

wherein: each $R^6$, $R^8$, $R^9$ and $R^{10}$ is independently hydrogen, hydroxyl, —(C$_1$-C$_6$)alkyl, —O(C$_1$-C$_6$)alkyl, —(C$_1$-C$_6$)alkylhalo, —OC(O)(C$_1$-C$_6$)alkyl, or halo; each $R^7$ is independently hydrogen, —(C$_3$-C$_8$)cycloalkyl, —(C$_6$-C$_{10}$)aryl, or —(C$_1$-C$_6$)alkyl(C$_6$-C$_{10}$) aryl; or a pharmaceutically acceptable salt thereof.

3. The method of claim 2 wherein each $R^6$, $R^8$, $R^9$, and $R^{10}$ group is independently hydrogen, —OH, —OCH$_3$, —CF$_3$, —CH$_3$, —OC$_2$H$_5$, —OC(O)CH$_3$, F, Cl, or Br.

4. The method of claim 2 wherein each $R^7$ group is independently hydrogen, —C$_2$H$_5$; -i-Pr, n-Pr, n-Bu, t-Bu, i-Bu, s-Bu, or cyclohexyl.

5. The method of claim 2 wherein each $R^6$, $R^8$, and $R^9$, is —OC(O)CH$_3$; each $R^7$ is i-propyl; and each $R^{10}$ is —CH$_3$.

6. The method of claim 1 wherein the chemosensitizing agent and the anticancer agent are administered at the same time.

7. The method of claim 1 wherein the chemosensitizing agent is administered prior to the anticancer agent.

8. The method of claim 1 wherein the anticancer agent is Flavopiridol, Adriamycin, Etoposide, Taxol, cisplatin or a combination thereof.

9. The method of claim 1 wherein the leukemia is acute lymphocytic leukemia, chronic lymphocytic leukemia, acute myelogenous leukemia, or chronic myelogenous leukemia.

* * * * *

SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: Synthetic construct

<400> SEQUENCE: 1

Asn Leu Trp Ala Ala Gln Arg Tyr Gly Arg Glu Leu Arg Arg Met Ser
1               5                   10                  15

Asp Lys Phe Val Asp
            20